(12) United States Patent
Viertl et al.

(10) Patent No.: US 7,535,565 B1
(45) Date of Patent: May 19, 2009

(54) SYSTEM AND METHOD FOR DETECTING AND ANALYZING COMPOSITIONS

(75) Inventors: John Ruediger Mader Viertl, Niskayuna, NY (US); Warren Arthur Nelson, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/970,785

(22) Filed: Jan. 8, 2008

(51) Int. Cl.
*G01J 3/30* (2006.01)
(52) U.S. Cl. .................................... 356/318
(58) Field of Classification Search ................. 356/318, 356/316; 385/12
See application file for complete search history.

(56) References Cited

U.S. PATENT DOCUMENTS

| | | | |
|---|---|---|---|
| 5,889,587 A * | 3/1999 | D'Silva et al. ............... | 356/316 |
| 6,147,754 A * | 11/2000 | Theriault et al. ............ | 356/318 |
| 6,762,836 B2 | 7/2004 | Benicewicz et al. | |
| 7,016,035 B2 | 3/2006 | Wu et al. | |
| 7,064,825 B2 | 6/2006 | Viertl et al. | |
| 2005/0221109 A1* | 10/2005 | Torigoe et al. .............. | 428/633 |

* cited by examiner

*Primary Examiner*—Kara E Geisel
*Assistant Examiner*—Abdullahi Nur
(74) *Attorney, Agent, or Firm*—Hartman & Hartman, P.C.; Gary M. Hartman; Domenica N.S. Hartman

(57) ABSTRACT

A system and method for performing laser plasma spectroscopy on a surface of a component, particularly to detect, analyze, and determine the extent of deposit build up on turbomachine components protected by coatings that are susceptible to damage from infiltration of deposits. The system includes a laser energy source and a probe interconnected with the laser energy source to receive a laser beam therefrom and then direct the laser beam onto the surface of the component and scan an area of the surface while the component remains stationary. The probe is further configured to collect radiation emitted from a laser-induced plasma generated by the laser beam at the surface of the component. The system is further equipped to transmit the radiation from the probe and spectrally analyze the radiation.

20 Claims, 3 Drawing Sheets

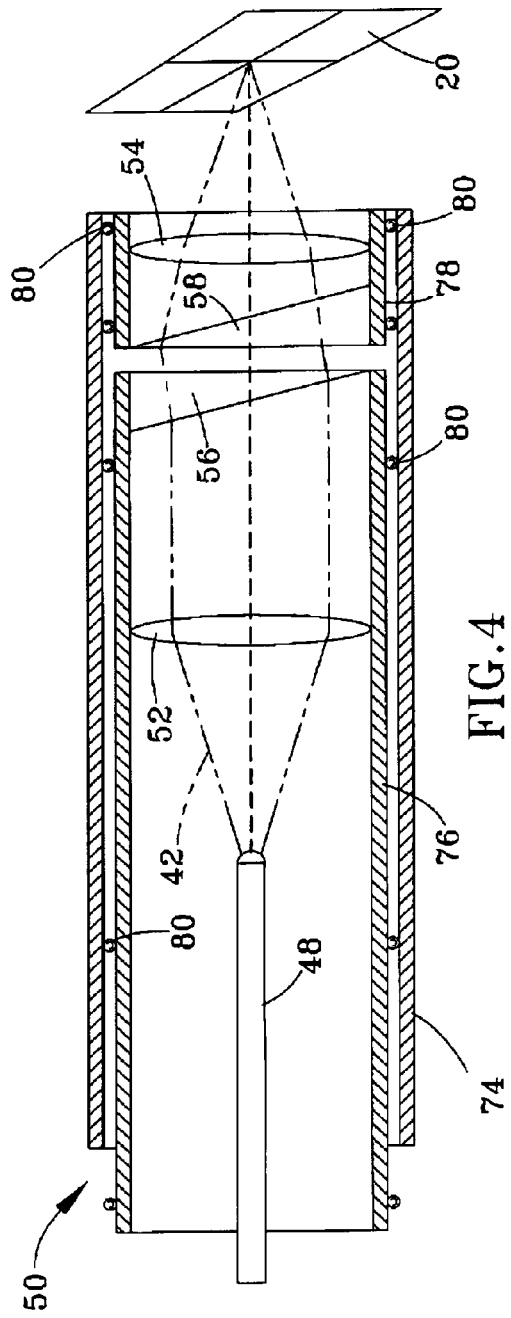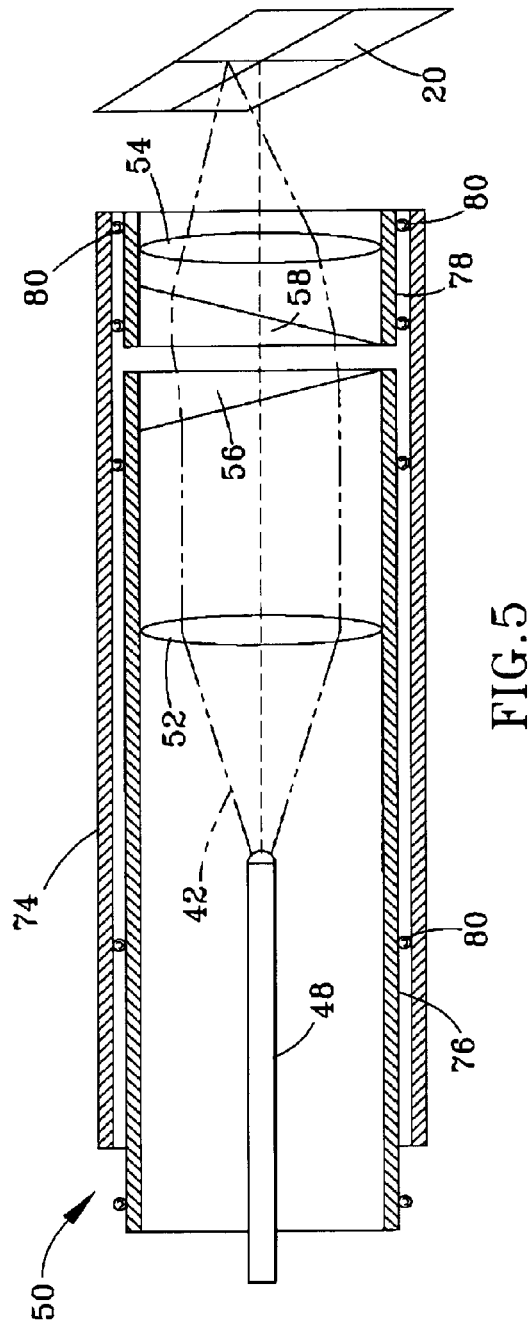

SYSTEM AND METHOD FOR DETECTING AND ANALYZING COMPOSITIONS

BACKGROUND OF THE INVENTION

This invention generally relates to systems and methods for detecting and analyzing compositions. More particularly, this invention is directed to a system and method for detecting, analyzing, and determining the extent of contaminant build up on components exposed to high temperatures, such as turbine components protected by coatings that are susceptible to damage by infiltration of contaminants in the operating environment of a turbomachine.

Hot section components of turbomachines, including gas turbines employed for power generation and propulsion, are often protected by a thermal barrier coating (TBC) to reduce the temperature of the underlying component substrate and thereby prolong the service life of the component. Ceramic materials and particularly yttria-stabilized zirconia (YSZ) are widely used as TBC materials because of their high temperature capability, low thermal conductivity, and relative ease of deposition by plasma spraying, flame spraying and physical vapor deposition (PVD) techniques. Plasma spraying processes such as air plasma spraying (APS) yield noncolumnar coatings characterized by a degree of inhomogeneity and porosity, and have the advantages of relatively low equipment costs and ease of application. TBC's employed in the highest temperature regions of turbomachines are often deposited by PVD, particularly electron-beam PVD (EBPVD), which yields a strain-tolerant columnar grain structure. Similar columnar microstructures with a degree of porosity can be produced using other atomic and molecular vapor processes.

To be effective, a TBC must strongly adhere to the component and remain adherent throughout many heating and cooling cycles. The latter requirement is particularly demanding due to the different coefficients of thermal expansion (CTE) between ceramic materials and the substrates they protect, which are typically superalloys, though ceramic matrix composite (CMC) materials are also used. An oxidation-resistant bond coat is often employed to promote adhesion and extend the service life of a TBC, as well as protect the underlying substrate from damage by oxidation and hot corrosion attack. Bond coats used on superalloy substrates are typically in the form of a diffusion aluminide coating or an overlay coating such as MCrAlX (where M is iron, cobalt and/or nickel, and X is yttrium, a rare earth element, or a reactive element). During the deposition of the ceramic TBC and subsequent exposures to high temperatures, such as during turbine operation, these bond coats form a tightly adherent alumina ($Al_2O_3$) layer or scale that adheres the TBC to the bond coat.

The service life of a TBC system is typically limited by a spallation event driven by bond coat oxidation, increased interfacial stresses, and the resulting thermal fatigue. In addition to oxide growth between the bond coat and TBC and CTE mismatch between the TBC (ceramic) and substrate (typically metallic), spallation can be promoted as a result of the TBC being contaminated with compounds present in the airflow of a turbomachine during its operation. Notable contaminants include varying mixtures of oxides such as calcia, magnesia, alumina and silica, whose presence becomes more prevalent when the ambient air contains particulates of dirt, volcanic ash, cement dust, and/or other materials containing these oxides. When present together at elevated temperatures, calcia, magnesia, alumina and silica can form a eutectic compound referred to herein as CMAS. CMAS has a relatively low melting temperature of about 1225° C. (and possibly less depending on its exact composition), such that during turbine operation the CMAS can melt and infiltrate the porosity within cooler subsurface regions of the TBC, where it resolidifies. As a result, during thermal cycling TBC spallation is likely to occur from the infiltrated and solidified CMAS interfering with the strain-tolerant nature of columnar TBC, particularly TBC deposited by PVD and APS due to the ability of the molten CMAS to penetrate their columnar and porous grain structures, respectively. Another detriment of CMAS is that the bond coat and substrate underlying the TBC are susceptible to corrosion attack by alkali deposits associated with the infiltration of CMAS. Finally, it should be noted that the likelihood of CMAS infiltration becomes greater as higher operating temperatures are used to increase the efficiency of turbomachines.

Various studies have been performed to find coating materials that are resistant to infiltration by CMAS. Notable examples are commonly-assigned U.S. Pat. Nos. 5,660,885, 5,683,825, 5,871,820, 5,914,189, 6,465,090, 6,627,323, 6,720,038 and 6,890,668, and U.S. Published Patent Application No. 2007/0116883. The protective coatings of these documents can be generally described as being impermeable, sacrificial, or non-wetting to CMAS. Impermeable coatings physically inhibit infiltration of molten CMAS, sacrificial coatings chemically inhibit infiltration by reacting with CMAS to increase its melting temperature and/or viscosity, and non-wetting coatings reduce the attraction between the solid TBC and the molten CMAS.

Notwithstanding the above advancements in coating technology, the ability to detect CMAS on TBC's of turbomachine components would be very desirable. However, a complication is that confirmation of the presence of CMAS requires chemical analysis, which using conventional equipment would require removal of the component from the turbine. Consequently, CMAS detection has typically been performed during regular maintenance schedules and based largely on visual observations. Accordingly there is an ongoing need for more convenient and less obtrusive techniques to detect the presence of CMAS. It would also be desirable if the capability existed to predict the useful life of the TBC and the component it protects based on the presence of CMAS.

BRIEF SUMMARY OF THE INVENTION

The present invention generally provides a system and method that perform laser plasma spectroscopy and are capable of detecting, analyzing, and determining the extent of CMAS build up on turbomachine components protected by coatings that are susceptible to damage from infiltration of CMAS at the elevated temperatures within the hot gas path of a turbomachine.

According to a first aspect of the invention, the system generally includes a laser energy source and a probe interconnected with the laser energy source to receive a laser beam therefrom. The probe comprises an outer member and at least first and second inner members within the outer member, with at least one of the first and second inner members being rotatable within the outer member. Each of the first and second inner members comprises a lens for focusing the laser beam and means for redirecting the laser beam prior to exiting the probe. The probe has an exterior configuration that enables the probe to be fixedly positioned sufficiently close to a turbomachine component to enable the laser beam exiting the probe to be directed onto the surface of the component and manipulated while the component is stationary to scan an area of the surface. The probe is further configured to collect radiation emitted from a laser-induced plasma generated by the laser beam at the surface of the component. Finally, the system further includes means for transmitting the radiation from the probe, and means for spectrally analyzing the radiation transmitted from the probe.

According to a second aspect of the invention, the method generally entails generating a laser beam with a laser energy source, transmitting the laser beam to a probe fixedly positioned adjacent a turbomachine component, operating the probe so that the laser beam exiting the probe is directed onto the surface of the component and is manipulated while the component is stationary to scan an area of the surface, collecting with the probe radiation emitted from a laser-induced plasma generated by the laser beam at the surface of the component, transmitting the radiation from the probe, and spectrally analyzing the radiation transmitted from the probe. The probe may be adapted to be inserted into the turbomachine through an opening, such as an existing sight hole port used to inspect the turbomachine with a borescope probe.

The system and method of this invention are preferably capable of rapid in-situ inspections and measurements performed on a component without causing life-limiting damage to the component. Inspection and analysis can be conducted during routine maintenance or inspection schedules when the turbomachine is not operating and is cool. Such inspections can be scheduled on the basis of the results of previous inspections and the operating conditions of the component since the previous inspection.

Other objects and advantages of this invention will be better appreciated from the following detailed description.

BRIEF DESCRIPTION OF THE DRAWINGS

FIGS. 4 and 5 schematically represent a beam focusing and steering probe suitable for use with the CMAS detection and analysis system of FIG. 2.

DETAILED DESCRIPTION OF THE INVENTION

Figure 1:
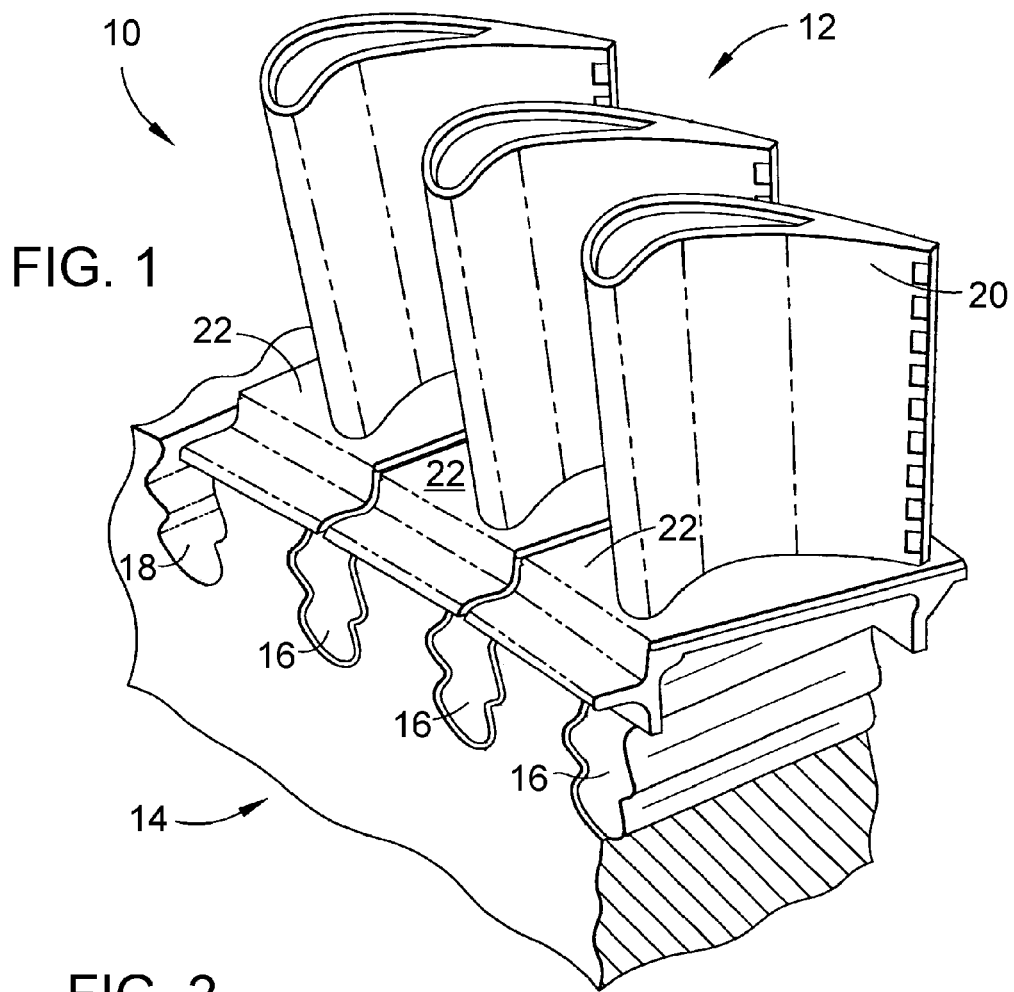
FIG. 1 is a fragmentary perspective view showing an example of a high pressure turbine disk with turbine blades mounted thereto.

The present invention will be described in reference to turbine components of a turbomachine, including gas turbines used for power generation and propulsion, though it should be understood that the invention can be employed with a variety of components that operate within thermally and chemically hostile environments. For purposes of discussion, a fragment of a high pressure turbine assembly 10 is shown in FIG. 1. The turbine assembly 10 is generally represented as being of a known type, and includes high pressure turbine blades 12 mounted to a disk 14. The blades 12 may be formed of an iron, nickel or cobalt-base superalloy, with nickel-base superalloys typically being preferred. The blades 12 are individually anchored to the turbine disk 14 with dovetails 16 that interlock with dovetail slots 18 formed in the circumference of the disk 14. Each blade 12 has an airfoil 20 and platform 22 against which hot combustion gases are directed during operation of the turbomachine, and whose surfaces are therefore subjected to severe attack by oxidation, hot corrosion and erosion, as well as contamination by CMAS.

Figure 2:
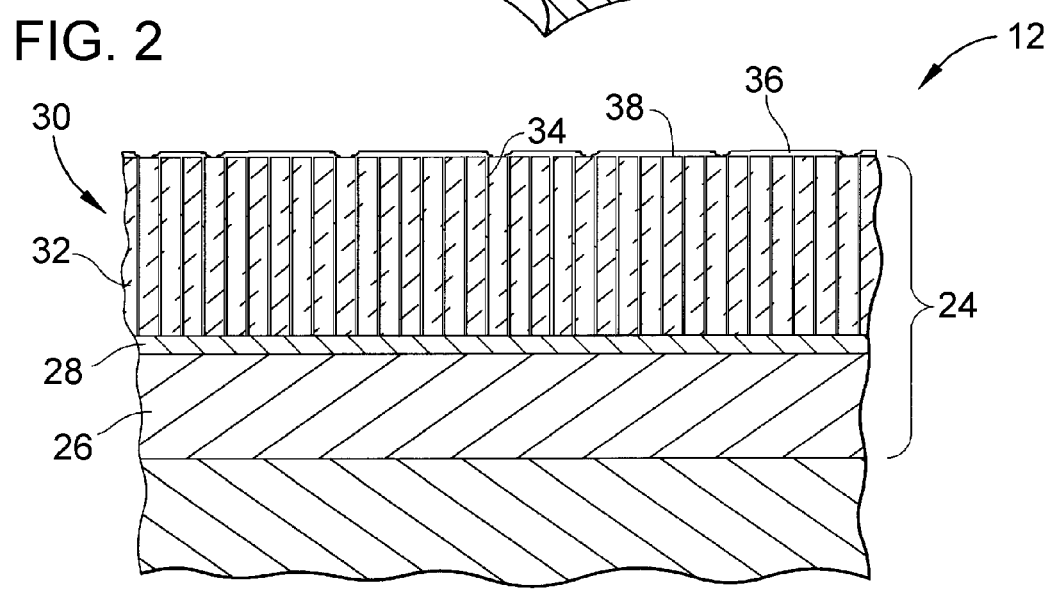
FIG. 2 is a fragmentary cross-sectional view of a thermal barrier coating (TBC) system on an airfoil surface of a blade shown of FIG. 1.

The surfaces of the airfoils 12 are protected by a TBC system 24, represented in FIG. 2 as including a metallic bond coat 26 that overlies the surface of the blade 12. As widely practiced with TBC systems for components of turbomachines, the bond coat 26 may be an aluminum-rich composition, such as an overlay coating of an MCrAlX alloy or a diffusion coating such as a diffusion aluminide or a diffusion platinum aluminide, all of which are well-known in the art. Aluminum-rich bond coats develop an aluminum oxide (alumina) scale 28, which grows as a result of oxidation of the bond coat 26. The alumina scale 28 chemically bonds a TBC 30, formed of a thermal-insulating material, to the bond coat 26. The TBC 30 of FIG. 2 is represented as having a strain-tolerant microstructure of columnar grains 32. As known in the art, such columnar microstructures can be achieved by depositing the TBC 30 using a physical vapor deposition (PVD) technique, such as EBPVD. The invention is also applicable to noncolumnar TBC deposited by such methods as plasma spraying, including air plasma spraying (APS). A TBC of this type is in the form of molten "splats," resulting in a microstructure characterized by irregular flattened (and therefore noncolumnar) grains and a degree of inhomogeneity and porosity. As with prior art TBC's, the TBC 30 of this invention is intended to be deposited to a thickness that is sufficient to provide the required thermal protection for the blade 12. A typical material for the TBC 30 is an yttria-stabilized zirconia (YSZ), such as a composition containing about 3 to about 8 weight percent yttria (3-8% YSZ), though other ceramic materials could be used, including but not limited to nonstabilized zirconia, or zirconia partially or fully stabilized by magnesia, ceria, scandia or other oxides.

Of particular interest to the present invention is the susceptibility of the TBC 30 to attack by CMAS, represented in FIG. 2 as deposits 36 on the surface 38 of the TBC 30. As discussed previously, CMAS is a relatively low melting compound that when molten is able to infiltrate porosity 34 formed by gaps, voids, etc., within columnar and noncolumnar TBC's, and subsequently resolidify to promote TBC spallation during thermal cycling. To address this problem, the present invention proposes a system and method for early detection of CMAS deposits on turbomachine hardware. The system and method advantageously can be employed without removing the blades 12 from the turbine, and can detect the presence of CMAS without damaging the TBC 30. In doing so, the present invention also provides the capability for predicting the useful life of the TBC 30 and, hence, the blade 12 it protects.

Figure 3:
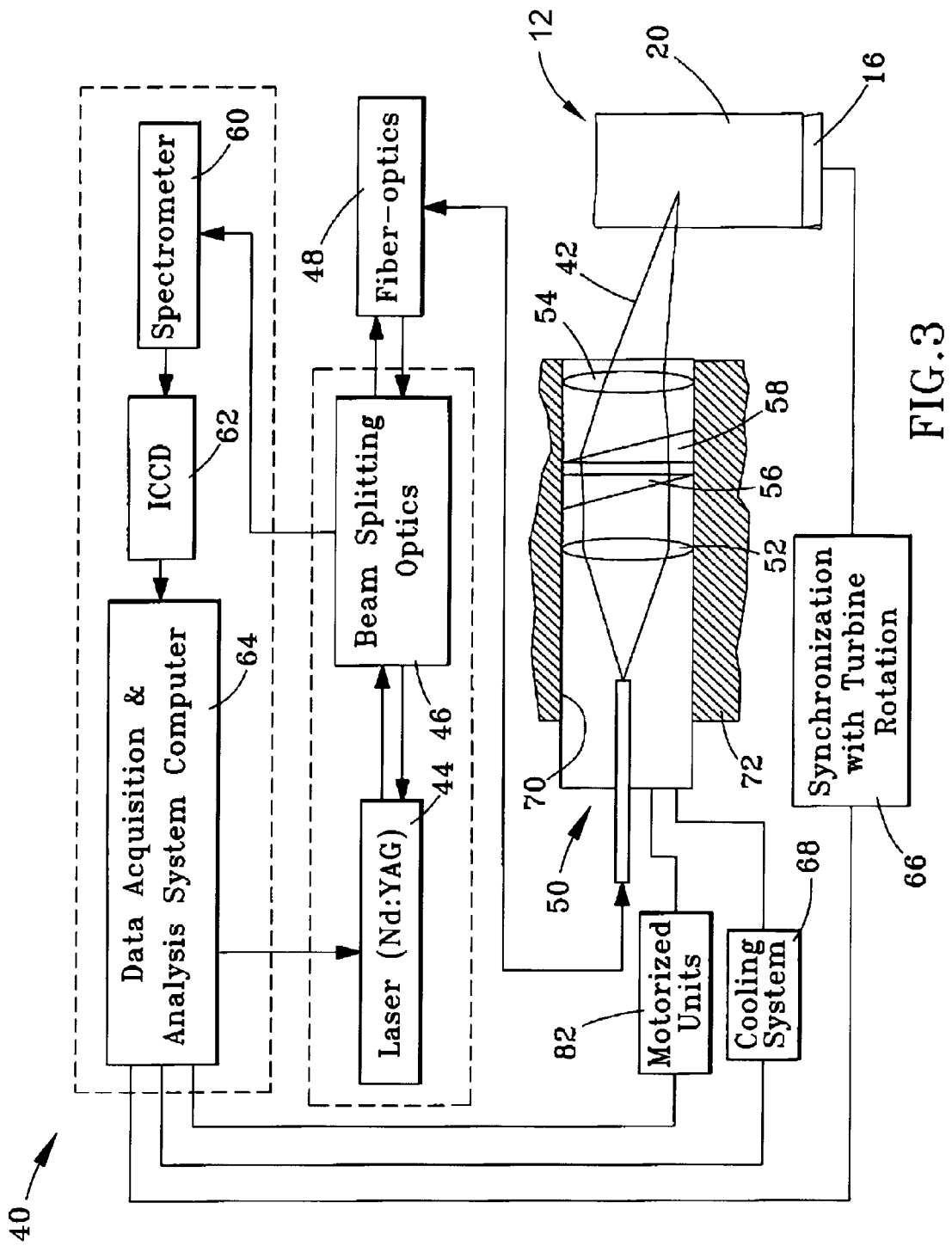
FIG. 3 schematically depicts a CMAS detection and analysis system in accordance with an embodiment of this invention.

FIG. 3 is a block diagram of a CMAS detection and analysis system 40 in accordance with an embodiment of the invention. The system 40 makes use of laser pulse spectroscopy (LPS), also known as laser-induced breakdown spectroscopy (LIBS) and laser-induced plasma spectroscopy (LIPS). As known in the art, LPS entails projecting a pulsed laser beam onto a material at a power density sufficient to vaporize (ablate) a small portion of the material and generate a luminous plasma that contains the characteristic atomic emission lines of elements within the material, which are then collected for spectral analysis. In FIG. 3, a laser beam 42 is represented as being projected in pulses onto a TBC-coated surface of a blade 12 (e.g., FIGS. 1 and 2), resulting in vaporization of a small portion of the TBC 30 and any deposits 36 on the TBC surface 38 (e.g., FIG. 2), and generating a luminous plasma (not shown). The LPS technique then utilizes the characteristic atomic emission lines (characteristic radiation) within the plasma to detect and analyze the composition of any deposits present on or within the TBC 30. The utilization of LPS techniques to analyze the compositions of coatings and coating deposits is disclosed in commonly-assigned U.S. Pat. Nos. 6,762,836 to Benicewicz et al., 7,016,035 to Wu et al., and 7,064,825 to Viertl et al., whose contents relating to the components and operation of LPS-based systems are incorporated herein by reference.

The present invention is concerned with CMAS deposits that may appear on various and relatively large surface regions of the blades 12, as well as other component surfaces within the hot gas path of a turbomachine. As such, a preferred aspect of the system 40 shown in FIG. 3 is the ability to project the laser beam 42 across relatively large surface regions of the TBC 30. According to another preferred aspect of the invention, the laser beam 42 can be directed at the blades 12 of the turbine assembly 10 while the blades 12 remain installed within turbine.

The system 40 is represented in FIG. 3 as generating the pulsed laser beam 42 with a Nd:YAG laser 44, which generates energy in the near infrared region of the electromagnetic spectrum. It is foreseeable that other laser generators could be employed, for example, of the Excimer (Excited dimer) type that generate energy in the visible and ultraviolet regions. From the laser 44, the beam 42 passes through beam splitting optics 46 before being delivered to the blade 12 via fiber optics 48, such as a coherent fiber bundle, and focused onto the surface of the blade 12 with a beam focusing and steering probe 50. As is typical in LPS systems, the laser 44 is operated to generate the laser light at its fundamental wavelength or any of its harmonic wavelengths, or otherwise any high peak power pulsed laser capable of generating sufficiently high focused intensities to vaporize and form a luminous plasma of the targeted material, which in this case is CMAS deposits 36 on the surface 38 of the TBC 30. As such, the primary elements to be detected are the oxides of calcium, magnesium, aluminum and silicon. Suitable laser beam power densities for this purpose are believed to be about 3 $GW/cm^2$ and greater. To facilitate its use while the turbine assembly 10 remains installed within a turbine, the laser 44 is preferably compact and portable, and is preferably contained within a light-impenetrable housing (not shown) to limit the risk of inadvertent exposure to the laser beam 42.

Following excitation with the laser beam 42 to generate the plasma, delayed spectroscopic measurements of the plasma are used to detect and measure the various specific transient species within the plasma. The laser beam 42 is preferably pulsed, such that multiple measurements are performed, with each measurement following a laser pulse. With knowledge of the original elements in the TBC 30 (such as zirconium, yttrium, and oxygen if formed of YSZ), the elements in the plasma can be detected and their amounts quantitatively determined by measuring the intensity of their characteristic atomic emission lines (characteristic radiation) emitted from the plasma. Detection and spectral analysis are performed by collecting the characteristic radiation emanating from the plasma with the probe 50, conducting the characteristic radiation back through the fiber optics 48 to the beam splitting optics 46, which directs the radiation to a high-speed digital spectrometer 60. The spectrometer 60 spectrally disperses and focuses the radiation onto an intensified charge-coupled device (ICCD) 62 or another suitable array detector, for example, a photo-diode array (PDA). A computer 64 can then be employed to display, store, and manipulate the spectral data obtained from the ICCD 62. The computer 64 is preferably capable of analyzing the emission spectra from multiple plasma events in real-time and display or save the data for future evaluation. Various commercial software packages for performing these operations are known and available for programming the computer 64, and will not be discussed in any detail here.

Implementation of the system 40 involves measuring and comparing the intensities of the unique wavelengths of the elemental constituents of CMAS, namely, calcium, magnesium, aluminum, and silicon. As such, the spectrometer 60 preferably has a spectral range for selectively tracking at least four elements, though the tracking of more elements is foreseeable. With proper correction for the natural differences in excitation efficacy, the ratio of the corrected intensities provides the ratio of these and other elements vaporized by the laser beam 42, enabling the stoichiometry of the CMAS deposits 36 to be ascertained. In addition to detecting and quantitatively measuring the amount and chemistry of CMAS deposits 36 present on the TBC 30, the characteristic spectra of the CMAS elements can be categorized as a function of the depth, from which the occurrence and possibly the extent to which CMAS has infiltrated the TBC 30 may also be determined. In any event, by combining the CMAS measurements with other available data, such as turbine operating hours, temperatures, etc., it is possible to predict the life of the TBC 30 and the blade 12 it protects based on the amount of CMAS deposits 36 present on the blade 12.

FIG. 3 further shows the computer 64 as being connected to a device 66 for synchronizing the operation of the system 40 with the rotation of the turbine assembly 10. The computer 64 and synchronization device 66 can control the system 40 so that the blades 12 can be individually and sequentially analyzed by the system 10 while the turbine assembly 10 is stationary, incrementally rotated, or continuously rotated. As such, the system 40 can perform an inspection during shutdown or operation of the turbomachine. The computer 64 is also shown coupled to a cooling system 68 to control the temperature of the probe 50. Such capabilities are optional but desirable in light of the preferred use envisioned for the system 40, in which the probe 50 is configured to be inserted into the turbine while shut down, such as through sight hole ports commonly found in the turbine walls of power generating turbines for inspection with a borescope, or additional inspection ports that can be installed for this purpose. In FIG. 3, the probe 50 is represented as being in a generally fixed position within a sight hole port 70 in a turbine wall 72, such that suitable manipulation of the laser beam 42 is desired to allow for examination of relatively broad surface regions of the blades 12. For this purpose, the probe 50 is represented as being an assembly that contain multiple sets of lenses 52 and 54 and beam deflectors 56 and 58, the latter of which are depicted as prisms though it will become apparent that other optical devices capable of redirecting the laser beam 42 could be used, including articulating mirror arrangements.

FIGS. 4 and 5 depict a configuration for the beam steering and focusing probe 50 with features capable of facilitating CMAS measurements on complex surfaces, such as the airfoils 20 of the blades 12. The probe 50 is represented as having an outer sleeve 74 that contains and supports two inner sleeves 76 and 78. The sleeves 74, 76, and 78 are preferably tubular-shaped, though not necessarily circular in cross-section. Furthermore, at least one and preferably both of the inner sleeves 76 and 78 are supported by bearings 80 that enable the sleeves 76 and 78 to rotate about their common axis with the outer sleeve 74 and linearly (longitudinally) translate within the outer sleeve 74. If the implementation shown in FIG. 3 is used, the outer sleeve 74 is preferably sized and configured for a close fit with the sight hole port 70. The fiber optic 48 is coupled to the first inner sleeve 76 and directs the laser beam 42 at the lens 52, which in turn focuses the beam 42 onto the beam deflector 56 based on well-known optic principles. As evident from FIGS. 4 and 5, the first set of lens 52 and beam deflector 56 is mounted within the first inner sleeve 76, and the second set of lens 54 and beam deflector 58 is mounted within the second inner sleeve 78, the latter of which is located at the distal end of the probe 50 located nearest the airfoil 20 when the probe 50 is mounted within the sight hole port 70.

By rotating and/or translating one or both inner sleeves 76 and 78, the beam deflectors 56 and 58 are able to cover a wide range of focal depths, and are further able to deflect and focus the beam 42 toward various locations on the surface of the airfoil 20, as evident by comparing FIGS. 4 and 5, and optionally even away from the airfoil 20. A table of parameters for focusing the beam 42 can be determined for use by the computer 64. If the position of the probe 50 relative to the blade 12 is known relative to an airfoil datum, CAD data for the airfoil 20 could be used to provide a running focus on the surface of the airfoil 20 as it is scanned with the beam 42 for CMAS deposits 36. In effect, a raster scanned region of the airfoil surface can be examined by the probe 50. Such a capability is particularly useful since CMAS infiltration and the ensuing damage is affected by the different temperature levels that exist over the surface of the airfoil 20 during turbine operation. With the knowledge of hot spots on the airfoil 20 during various operating conditions of the turbine, the probe 50 can be employed to specifically examine certain surface areas of the airfoil 20 that are likely to be most prone to CMAS deposits 36.

The probe 50 can be equipped with motorized units 82 (FIG. 3) that are controlled by the computer 64 to rotate and linearly translate the sleeves 76 and 78 within the outer sleeve 74 and relative to each other. In this manner, the computer 64 can be utilized to focus the beam 42 at different focal lengths by linearly moving the inner sleeves 76 and 78 relative to each other, and steer the beam 42 by rotating one or both inner sleeves 76 and 78 relative to each other, with the result that the probe 50 is capable of performing a large variety of scans. For example, if the two inner sleeves 76 and 78 are controlled by the computer 64 to rotate at the same rate in opposite directions, the beam 42 performs a line scan on the surface of the airfoil 20. If the sleeves 76 and 78 rotate in the same direction (either clockwise or counterclockwise) but at different rates, the beam 42 can be manipulated to perform a spiral or otherwise generally circular scan. By stepping the scan rates, the scan performed by the beam 42 can be in a pattern comprising a series of rings. Those skilled in the art will appreciate that additional scan patterns are also possible and within the scope of this invention as a result the capability of rotating and linearly translating the sleeves 76 and 78 in the same direction, in opposite directions, at the same rate, and at different rates relative to each other.

Those skilled in the art will also appreciate that if mirrors are used in place of the prisms for the beam deflectors 56 and 58, the orientations of the deflectors 56 and 58 would differ from that shown in FIGS. 4 and 5, though the overall concept of manipulating the beam 42 to scan the surfaces of the airfoils 20 would remain the same. With the use of mirrors, an orthogonal mirror would be further employed to deflect the beam 42 in a plane perpendicular to the plane represented in FIGS. 4 and 5.

In view of the above, it can be appreciated that the system 40 and its probe 50 can be used to detect, measure, and assess the severity of CMAS deposits 36 on the turbine blades 12 (as well as other hot gas path components of the turbine), without limitation to regular maintenance schedules and without relying simply on visual observations. Instead, the system 40 and probe 50 provide a basis for changing CMAS inspection schedules from maintenance-based to condition-based. With knowledge of changes in amounts and locations of CMAS deposits 36, as well as any chemical profiles of the CMAS deposits 36 and any other deposits, it is foreseeable that one could adjust the thermal profiles in a turbomachine to minimize the generation of the CMAS melt that leads to TBC spallation and, ultimately, component failure.

Advantageously, the system 40 and probe 50 can typically perform the desired analysis using a series of small pulses, with the amount of material removed being adjustable by the intensity and number of laser pulses used at any given location. It is envisioned that suitable results can be obtained by vaporizing about one nanometer of material from a surface region of about 20 mils (about 0.5 mm) in diameter, though greater and lesser amounts are also possible. The surface analysis can be performed without the need for surface preparation. Consequently, notable potential advantages of this invention can include the capability for rapid in-situ inspections and measurements performed on components within a turbomachine without causing life-limiting damage to the components. Such inspections can be scheduled on the basis of the results of previous inspections and the operating conditions of the turbomachine since the previous inspection. Furthermore, the system 40 and its probe 50 can be configured to allow for remote operation of the probe 50.

While the invention has been described in terms of particular embodiments, it is apparent that other forms could be adopted by one skilled in the art. For example, it is foreseeable that functionally-equivalent devices and equipment could be used in place of the devices and equipment noted and described in reference to the disclosed embodiments. Furthermore, the disclosed invention is not limited to detecting CMAS deposits are turbomachine components, but could find application in other circumstances where spectral analysis of a surface is desired. Accordingly, the scope of the invention is to be limited only by the following claims.

The invention claimed is:

1. A system for performing laser plasma spectroscopy on a surface of a component, the system comprising:
    a laser energy source;
    a probe interconnected with the laser energy source to receive a laser beam therefrom, the probe comprising an outer member and at least first and second inner members within the outer member, at least one of the first and second inner members being rotatable within the outer member, each of the first and second inner members individually comprising a lens for focusing the laser beam and means for redirecting the laser beam prior to exiting the probe, the probe having an exterior configuration that enables the probe to be fixedly positioned sufficiently close to the component to enable the laser beam exiting the probe to be directed onto the surface of the component and manipulated by relative movement of the first and second inner members while the component is stationary to scan an area of the surface over a range of focal depths, the probe being configured to collect radiation emitted from a laser-induced plasma generated by the laser beam at the surface of the component;
    means for transmitting the radiation from the probe; and
    means for spectrally analyzing the radiation transmitted from the probe.

2. The system according to claim 1, wherein the transmitting means transmits the laser beam from the laser energy source to the probe.

3. The system according to claim 1, wherein the lens of the first inner member focuses the laser beam onto the redirecting means of the first inner member, the redirecting means of the first inner member directs the laser beam onto the redirecting means of the second inner member, and the redirecting means of the second inner member directs the laser beam onto the lens of the second inner member.

4. The system according to claim 1, further comprising means for operating the lens and the redirecting means of the probe to scan the laser beam onto the component in multiple different patterns.

5. The system according to claim 4, wherein the operating means is operable for individually rotating and linearly translating the first and second inner members.

6. The system according to claim 4, wherein the operating means comprises a motorized unit operable for rotating and linearly translating the first and second inner members in the same direction, in opposite directions, at the same rate, and at different rates.

7. The system according to claim 1, wherein the transmitting means projects the laser beam onto the lens of the first inner member.

8. The system according to claim 1, wherein the surface of the component is defined by a coating, the laser energy source and the probe are cooperatively adapted to vaporize a deposit on the coating, and the spectral analyzing means is adapted to selectively detect and chemically analyze the deposit and quantitatively measure the deposit.

9. The system according to claim 8, wherein the deposit contains oxides of calcium, magnesium, aluminum, and silicon.

10. A system for performing laser plasma spectroscopy on a surface of a turbine component of a turbomachine, the system comprising:
a laser energy source;
a probe interconnected with the laser energy source to receive a laser beam therefrom, the probe comprising an outer member and at least first and second inner members within the outer member, at least one of the first and second inner members being rotatable within the outer member, each of the first and second inner members comprising a lens for focusing the laser beam and means for redirecting the laser beam prior to exiting the probe, the probe having an exterior configuration that enables the probe to be fixedly positioned sufficiently close to the component to enable the laser beam exiting the probe to be directed onto the surface of the component and manipulated while the component is stationary to scan an area of the surface, the probe being configured to collect radiation emitted from a laser-induced plasma generated by the laser beam at the surface of the component;
means for transmitting the radiation from the probe; and
means for spectrally analyzing the radiation transmitted from the probe;
wherein the probe is configured to be mounted in a port of the turbomachine.

11. A method of performing laser plasma spectroscopy on a surface of a component, the method comprising:
generating a laser beam with a laser energy source;
transmitting the laser beam to a probe fixedly positioned adjacent the component;
operating the probe so that the laser beam is manipulated by relative movement of at least two redirecting means within the probe to cause the laser beam to scan an area of the surface after the laser beam exits the probe and is directed onto the surface of the component while the component is stationary;
collecting with the probe radiation emitted from a laser-induced plasma generated by the laser beam at the surface of the component;
transmitting the radiation from the probe; and spectrally analyzing the radiation transmitted from the probe.

12. The method according to claim 11, wherein the operating step comprises scanning the laser beam onto the component in multiple different patterns.

13. The method according to claim 11, wherein the probe comprises an outer member and at least first and second inner members within the outer member, the first and second inner members respectively comprise a first and a second of the at least two redirecting means, and the operating step comprises at least one of rotating and linearly translating at least one of the first and second inner members within the outer member.

14. The method according to claim 13, wherein the operating step further comprises using a lens of the first inner member to focus the laser beam onto the first redirecting means of the first inner member, using the first redirecting means to direct the laser beam onto the second redirecting means of the second inner member, and using the second redirecting means of the second inner member to direct the laser beam onto a lens of the second inner member, and wherein the lenses of the first and second inner members are operable to cause the first and second redirecting means to cover a range of focal depths.

15. The method according to claim 14, wherein the operating step further comprises selectively rotating and linearly translating the first and second inner members according to at least one of the following: in the same direction, in opposite directions, at the same rate, and at different rates.

16. The method according to claim 11, wherein the surface of the component is defined by a coating, the laser beam vaporizes a deposit on the coating, and the radiation is spectrally analyzed to detect and chemically analyze the deposit and quantitatively measure the deposit.

17. The method according to claim 16, wherein the deposit contains oxides of calcium, magnesium, aluminum, and silicon.

18. The method according to claim 17, further comprising detecting the extent to which the deposit has infiltrated porosity within the coating.

19. The method according to claim 18, wherein the coating is a thermal barrier coating.

20. A method of performing laser plasma spectroscopy on a surface of a turbine component of a turbomachine, the method comprising:
generating a laser beam with a laser energy source;
transmitting the laser beam to a probe fixedly positioned adjacent the component;
operating the probe so that the laser beam exits the probe, is directed onto the surface of the component, and is manipulated while the component is stationary to scan an area of the surface;
collecting with the probe radiation emitted from a laser-induced plasma generated by the laser beam at the surface of the component;
transmitting the radiation from the probe;
spectrally analyzing the radiation transmitted from the probe; and
detecting the extent to which the deposit has infiltrated porosity within the coating;
wherein the surface of the component is defined by a thermal barrier coating, the laser beam vaporizes a deposit on the coating, the radiation is spectrally analyzed to detect and chemically analyze the deposit and quantitatively measure the deposit, the deposit contains oxides of calcium, magnesium, aluminum, and silicon, and the probe is mounted in a port of the turbomachine.

* * * * *